(12) United States Patent
Shelley et al.

(10) Patent No.: US 7,915,586 B2
(45) Date of Patent: *Mar. 29, 2011

(54) METHOD FOR PERFORMING MID-IR SPECTROSCOPY MEASUREMENTS TO MEASURE FILM COATING THICKNESS, WEIGHT AND/OR FILM COMPOSITION

(75) Inventors: Paul H. Shelley, Lakewood, WA (US); Gregory J. Werner, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/189,045

(22) Filed: Aug. 8, 2008

(65) Prior Publication Data

US 2010/0032571 A1    Feb. 11, 2010

(51) Int. Cl.
*G01N 21/35* (2006.01)
(52) U.S. Cl. .......... 250/339.11; 250/339.08; 250/339.09
(58) Field of Classification Search ............. 250/339.11, 250/339.09, 339.08
See application file for complete search history.

(56) References Cited

U.S. PATENT DOCUMENTS

| | | | | |
|---|---|---|---|---|
| 5,900,633 A * | 5/1999 | Solomon et al. | .......... | 250/339.08 |
| 6,184,528 B1 * | 2/2001 | DiMarzio et al. | ........ | 250/339.08 |
| 6,984,825 B2 * | 1/2006 | Shelley et al. | ............ | 250/339.11 |
| 7,068,363 B2 * | 6/2006 | Bevis et al. | ................ | 356/237.5 |
| 2004/0023403 A1 * | 2/2004 | Tatsunari | ...................... | 436/144 |
| 2010/0032572 A1 * | 2/2010 | Shelley et al. | ............. | 250/341.8 |

\* cited by examiner

*Primary Examiner* — Constantine Hannaher
(74) *Attorney, Agent, or Firm* — Tung & Associates

(57) ABSTRACT

A method of determining a film coating thickness on a substrate and/or amount one or more compositional ingredients of said film coating including making mid-IR spectra of a series of coating thickness or coating weight standards (and/or composition standards) on an appropriate substrate material to match sample material in question, pre-processing the data to prepare it for multivariate calibration methods, performing the multivariate calibration, saving the calibration model in the hand-held mid-IR device in an appropriate format, and using the calibration model to predict sample material in question from their mid IR spectra.

10 Claims, 4 Drawing Sheets

METHOD FOR PERFORMING MID-IR SPECTROSCOPY MEASUREMENTS TO MEASURE FILM COATING THICKNESS, WEIGHT AND/OR FILM COMPOSITION

FIELD OF THE INVENTION

This invention generally relates to Infrared (IR) measurement methods and apparatus, and more particularly provides a method for performing non-destructive Mid-IR spectroscopy measurements of surface characteristics of materials including determining a thickness and/or composition of a film coating on a substrate, including bond primer thickness (coating weight) and/or bond primer composition on a metallic substrate.

BACKGROUND OF THE INVENTION

IR spectroscopy measurements may be useful for a variety of purposes including aerospace, automotive and industrial applications, as well as biological and bio-medical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety of organic as well as inorganic materials.

For example, frequently it is necessary to determine the thickness of a coating material on a substrate, to verify that the film coating thickness is sufficiently thick and/or to verify that the film has the proper composition, including but not limited to, bond primer film thicknesses on a metallic substrate.

One problem with determining the thickness of thin films on substrates may include the fact that the surface may include surface roughness, making surface contact methods that contact the surface over the scale of the roughness, such as eddy current measurement methods, inadequate. In addition, the film may be sufficiently thin to make prior art methods such as eddy current detection methods inadequate.

Other non-destructive methods in the prior art used to measure the properties of thin films includes using IR absorbance to determine the amount of a chromated conversion coating on a metallic substrate (U.S. Pat. No. 6,794,631, determining the amount of an anodize coating on a metallic substrate, (U.S. Pat. No. 6,784,431), determining an amount of chemical cure and amount of surface contamination, determining the amount/thickness of an opaque coating on a substrate (U.S. Pat. No. 6,903,339) and (U.S. Pat. No. 7,223,977), and determining an amount of heat damage to a resin-fiber composite substrate (U.S. Pat. No. 7,115,869), all of which are fully incorporated by reference herein.

None of the above methods and associated devices, however, disclose a method or device that is suitable for performing IR spectroscopy including determining a thickness and/or composition of a thin film coating on a substrate, particularly where a portable, real-time capability is desirable, such as in aircraft manufacturing, assembly, maintenance, and repair of aircraft.

Thus, there is a continuing need for improved IR non-destructive testing methods including a method that is suitable for performing IR spectroscopy to determine a thickness (or coating weight) and/or composition of a film coating on a substrate, including a portable, real-time IR spectroscopic method, advantageously useable in aircraft manufacturing, assembly, maintenance, and repair of aircraft.

Therefore it is an object of the invention to provide a method that is suitable for performing IR spectroscopy to determine a thickness (or coating weight) and/or composition of a film coating on a substrate, including a portable, real-time IR spectroscopic method, advantageously useable in aircraft manufacturing, assembly, maintenance, and repair of aircraft.

SUMMARY OF THE INVENTION

The present invention includes methods of determining a film coating thickness on a substrate including obtaining the mid IR spectra of a series of film coating thickness (or weight) standards and building a multivariate calibration model with the spectra of those standards. An infrared spectrum obtained from the coating film which is in question can then be predicted by the multivariate model to determine the thickness (or weight) of the film.

These and other objects, aspects and features of the invention will be better understood from a detailed description of the preferred embodiments of the invention which are further described below in conjunction with the accompanying Figures.

DETAILED DESCRIPTION OF THE PREFERRED EMBODIMENT

The present invention achieves the foregoing objects, aspects and features by providing a method of non-destructively determining the thickness of a film coating on a substrate where the method may be accomplished by making an infrared (IR) spectroscopy measurement with an IR spectrometer over a spectrum of wavelengths in the mid-IR, preferably with a portable mid-IR spectrometer, and performing multivariate calibration of mid-IR spectra to a series of coating thickness (or coating weight) standards in order to generate a calibration model that can be used to predict the coating thickness (or coating weight) for samples in question including as part of an manufacturing, assembly, maintenance, or repair process of an aircraft. It is noted the terms 'coating thickness (or coating weight)' refers to a film coating thickness that may alternatively be expressed in terms of weight per unit area (e.g., mg/ft$^2$) or a conventional length unit (e.g., microns).

It will be appreciated that although the invention is particularly explained with reference to using IR spectroscopy to determine a thickness and/or composition of a film coating on a material surface (including roughened metallic surfaces) used in portions of aircraft, that the invention may additionally be advantageously used to quantify a thickness and/or composition of a film coating on material surfaces in general.

While either a portable or non-portable IR spectrometer may be used to carry out the mid-IR spectroscopy measurements according to the present invention, and the spectrum of wavelengths used to make the mid-IR spectroscopy measurements may include all or a portion of the wavelengths between about 400 and about 4000 wavenumbers (cm$^{-1}$) (25 to 2.5 microns) more preferably between about 650 and about 4000 wavenumbers (cm$^{-1}$) (15.4 to 2.5 microns). In a preferred embodiment, a hand-held portable spectrometer capable of performing Fourier Transform IR (FT-IR) spectroscopy measurements over the mid-IR range of wavelengths outlined above is used to perform the IR spectroscopy measurements according to the present invention.

The hand-held portable FT-IR spectrometer may have the capability to supply source IR energy to a sample at a predetermined incident angle between about 30 to about 60 degrees, and collect reflected light from the sample through a broad range of angles which may exclude the incident angle. The hand-held portable IR device preferably has the ability to make diffuse reflectance IR spectroscopic measurements (also referred to as an external reflectance IR spectroscopic measurement.

Figure 1:
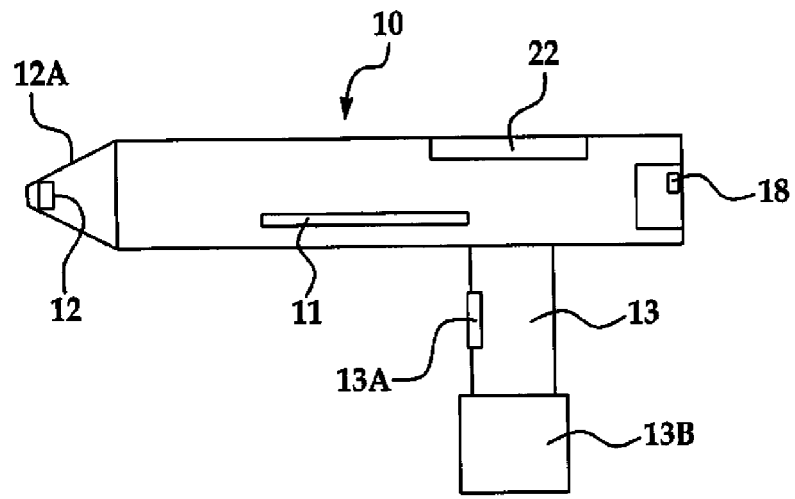
FIG. 1 is a schematic diagram of an exemplary hand-held portable mid-IR spectrometer suitably used to make mid-IR spectroscopy measurements according to an embodiment of the invention.

Referring to FIG. 1 is shown a side view of a portable (handheld) IR spectrometer 10 according to an embodiment of the invention. The portable IR spectrometer 10 may have the capability of performing near-IR and/or mid-IR spectroscopy measurements, and in a preferred embodiment at least has the capability of performing mid-IR (FT-IR) spectroscopy measurements. By the term 'hand-held portable' is meant an instrument that may be easily carried and picked up and move about to make IR spectroscopy measurements by an average person, e.g., has a weight of less than about 8 pounds and may be hand-held and aimed (or held against) a location on the measurement surface to make a spot-size measurement.

The portable IR spectrometer 10 also preferably includes a microprocessor and memory (e.g. micro-processor board 11) and may be interfaced (placed in communicated with) with other computing devices (e.g., USB port 18). The portable IR spectrometer 10 may be supplied power by one or more batteries (e.g., 13B in handle portion 13). The portable IR spectrometer 10 is preferably programmable and/or capable of accepting, storing, and executing preprogrammed instructions for carrying out IR spectroscopy measurements. The portable IR spectrometer 10 preferably has the capability to provide incident IR light (energy) and collect reflected mid-IR spectra over all or portions of an operating wavelength range (e.g., 400 wavenumbers (cm$^{-1}$) to about 4000 wavenumbers (cm$^{-1}$)) and to store the spectra and perform mathematical manipulation of the data comprising the spectra including performing multivariate analysis of the spectra.

In one embodiment, the portable IR spectrometer 10 preferably has an elongated front portion 12A which contains an one or more IR transparent energy windows e.g., 12, for example the front portion 12A may have a nose-like or snout-like (probe) shape, which advantageously aids in the aiming and positioning of the portable IR spectrometer 10 with respect to a measurement surface to make a spot size IR spectroscopy measurement of a pre-defined size. For example, an IR-transparent window 12, may be set back from the surface of the nose portion 12A, which may be placed on or close to the surface of the sample to be measured to produce a known spot-size measurement area, e.g., which may be any size but preferably ranges from an area of about 1 mm$^2$ to about 1 cm$^2$. In some embodiments, the nose portion 12A may be an interchangeable IR probe, including different IR spectrum ranges and/or measurement spot sizes, and may include IR transparent fiber optics.

The portable IR spectrometer 10 may include a triggering device e.g. 13A on handle portion 13 for triggering an IR spectroscopy or the IR spectroscopy measurement may be alternately triggered e.g., by softkeys on an interactive LCD touchscreen 22. It will be appreciated that the portable IR spectrometer 10 may be of any suitable ergonomic shape to enhance the portability and ease of holding and manipulating the spectrometer to carryout hand-held IR spectroscopy measurements.

The portable IR spectrometer 10 preferably has the ability to store collected IR spectra and perform mathematical manipulation of the data comprising the spectra including multivariate analysis of the spectra. The portable IR spectrometer 10 may include interactive buttons and/or softkeys e.g., on an interactive LCD or LED touchscreen 22, or elsewhere, and may include a textual display to guide the operator through an IR spectroscopy measurement process.

In addition, suitable calibration background reference standard materials and wavelength reference standard materials may be provided for calibrating the IR spectrometer prior to performing IR spectroscopy measurements according to embodiments of the invention.

In one embodiment, an IR spectrometer used to carry out an IR spectroscopy measurement according to the present invention, such as the portable IR spectrometer 10, may be provided and have stored in memory one or more calibration algorithms for IR spectra for use in a subsequent IR spectroscopy measurement and multivariate prediction processes where the IR spectra to be predicted is made with respect to material in a similar condition to an area of the sample with a known level (e.g. baseline including the absence of), the property to be measured, such as the absence of a bond primer film coating on a roughened metallic substrate. For example, it has been found that wavelengths in the mid-IR range, as noted above, are particularly useful for determining the thickness of an organic material such as bond primer on a metallic surface, including a roughened metallic surface and as well as determining one or more compositional ingredients of the film.

In addition, a previously determined multivariate calibration of IR spectra versus thickness of a film coating may be stored in memory within the IR spectrometer. For example, the predetermined calibration may be determined by calibrating to a plurality of model IR spectra (absorbance and/or reflectance at multiple wavelengths) with a known thickness (or weight/area) of model bond primer film coatings from a respective plurality of model samples where the known thickness (or weight/area including one or more compositional ingredients) for each of the model samples is determined by separate and independent measurements, e.g., optical or electron microscopy.

As such, an IR spectrometer, such as portable IR spectrometer 10, may be calibrated such that an in-situ (real-time) analysis of collected IR spectra taken from an actual sample may be performed to determine a thickness and/or amount of one or more compositional ingredients of the film coating.

For example, the calibration may be done on an external computer and the resulting calibration model may be downloaded to the hand-held mid-IR system. Preferably, a quantified (numerical) level of the film coating thickness and/or amount of one or more compositional ingredients may be determined in real-time by a portable IR spectrometer, such as the IR spectrometer 10, and stored and/or output. Additionally or alternatively, a pass/fail type determination (thickness and/or compositional ingredient above or below a threshold numerical value) and resulting indication thereof may stored and/or output.

The portable IR spectrometer 10, or another IR spectrometer used to carry out IR spectroscopy measurements according to embodiments of the invention, preferably includes a computer processor capable of multivariate analysis of the IR spectra or the calibration may be done on an external computer (controller) and the resulting calibration model downloaded to the hand-held mid-IR system. For example, the IR spectrometer (or an associated computer/controller) preferably has the ability to mathematically and statistically correlate and determine changes in a plurality of variables (e.g., IR spectra including reflectance at a plurality of wavelengths) with respect to one or more reference IR spectra. In addition, multivariate statistical approaches may be used to correlate the statistically determined changes in the plurality of variables (e.g., absorbance and/or reflectance at one or more wavelengths) with one or more second variables or (e.g. a change in a separately measured material property (such as thickness or an amount of one or more compositional ingredients) that is correlated by multivariate analysis to relative changes in the sample IR spectra.

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches include classification methodologies, such as, linear discriminant analysis ("LDA"), cluster analysis (e.g., k-means, C-means, etc., both fuzzy and hard), and neural network ("NN") analysis.

Further, it will be appreciated that there are several data processing methods that may be suitably used to in connection with suitable multivariate statistical approaches including smoothing, taking first and second derivatives of the IR spectra, and peak enhancement methods.

In addition, multivariate analysis of collected IR spectra may include the selection and clustering together of groups of wavelengths on which to perform a regression analysis to determine a corresponding change in the IR spectra (spectrum) (e.g., reflectance) with respect to reference spectra (spectrum). It will be appreciated that an individual IR spectrum may be formed from several IR spectra (e.g., by averaging techniques known in the art). In addition, the raw IR spectra may be transformed into second IR spectra by taking first and/or second derivatives and performing smoothing and/or peak enhancement as well as carrying out regression analysis. For example, manipulation the raw IR spectra by smoothing algorithms prior to or following taking a first derivative and then quantifying a degree of change of the IR spectra from a reference spectrum (similarly processed) according to a regression or partial lest squares analysis may be performed.

In addition, the IR spectroscopy measurement process may include collecting reference IR spectra (including calculated absorbance and/or reflectance) which may serve as a baseline from which to determine relative changes in sample IR spectra by multivariate analysis. In addition, various processing methods as are known in the art may be used to form a single IR spectrum from a collection of a plurality of collected IR spectra, including various averaging techniques, for example to improve a signal to noise ratio, prior to carrying out multivariate analysis to determine a change from reference spectrum. It will be appreciated that the change may include a change at one or more wavelengths including clusters of wavelengths.

Figure 2A:
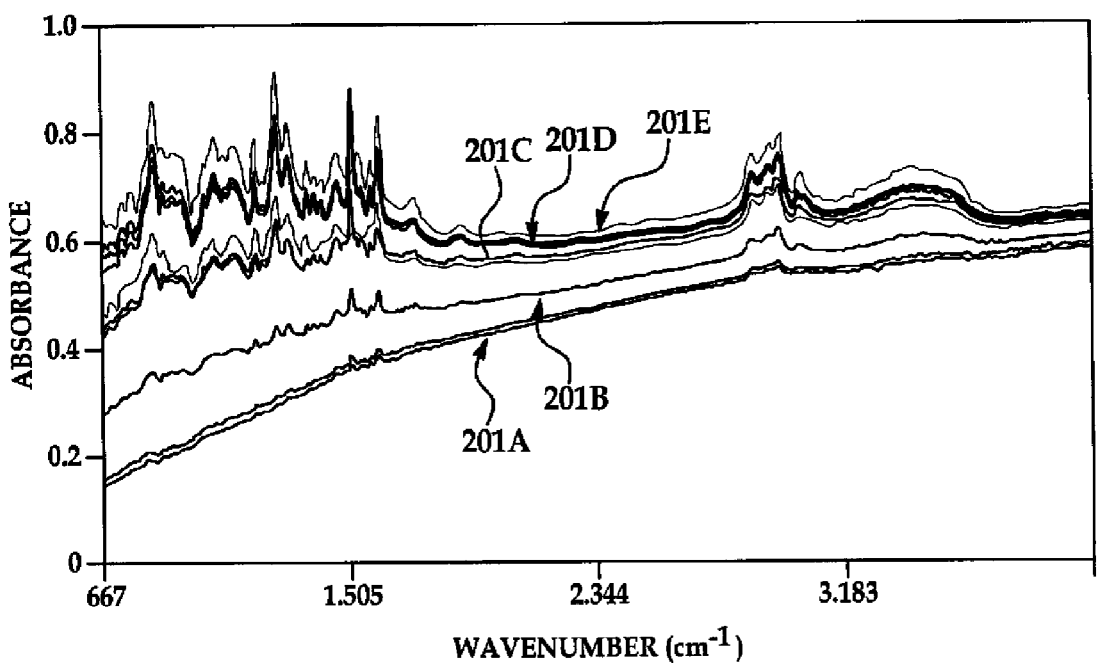
FIG. 2A shows exemplary raw mid-IR spectra used for multivariate calibration according to an embodiment of the invention.
Figure 2B:
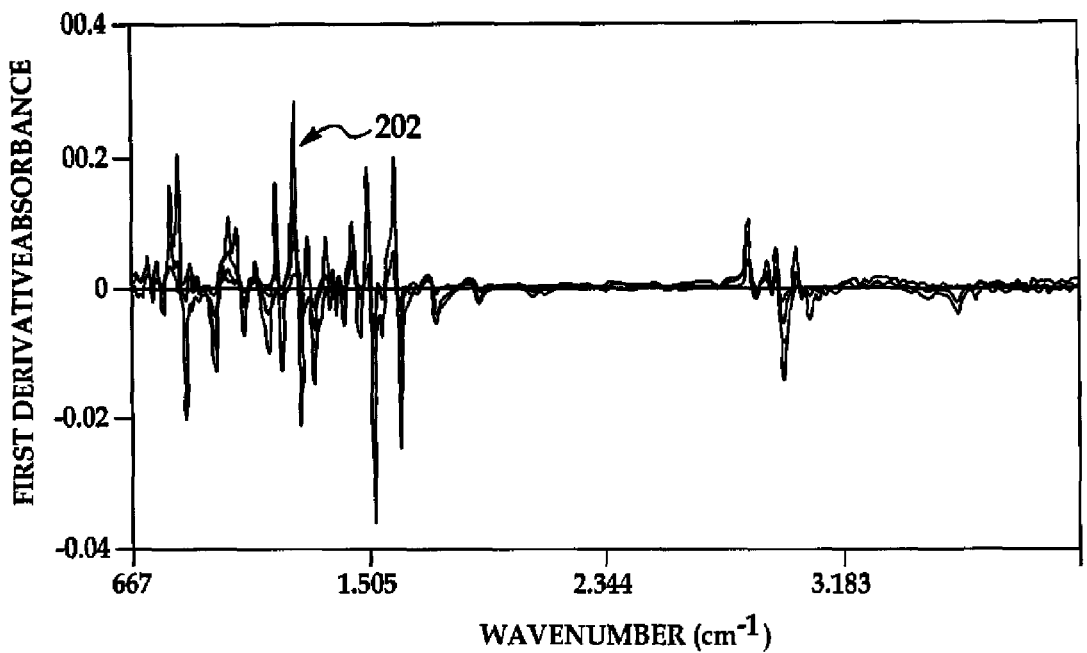
FIG. 2B shows pre-processed mid-IR spectra using a first derivative and smoothing algorithm.

Referring to FIG. 2A is shown a series of exemplary IR spectra 201A, 201B, 201C, 201D, and 201E for a series of weight/area sample/standards (showing multiple of FTIR scans/spectra for each sample/standard) following transformation of the raw sample FT-IR spectra show Absorbance vs. wavenumber ($cm^{-1}$) for a bond primer coating on grit blasted titanium. FIG. 2B shows sample/standard spectra 202 after taking a first derivative, employing a smoothing algorithm (e.g., $1^{st}$ derivative with 7 point smoothing), prior to performing a multivariate calibration which may include multiple spectra on each coating standard, and may use partial least squares to determine the calibration model that can be used to predict the coating thickness or coating weight (per unit area) of samples in question.

Figure 2C:
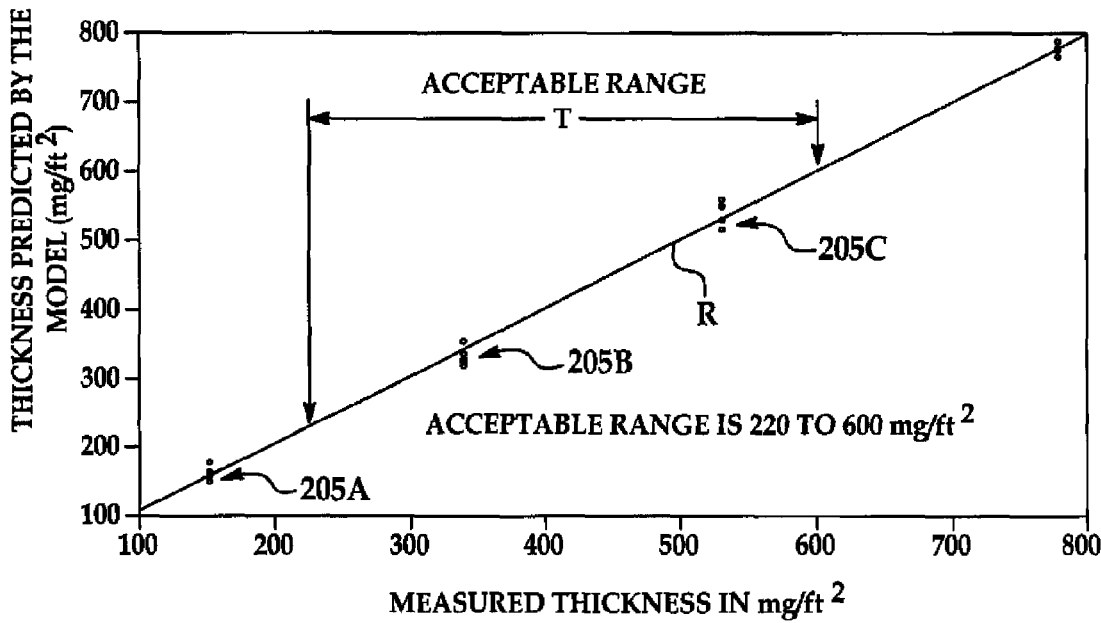
FIG. 2C shows data points for an exemplary conceptual predetermined calibration for a series of several bond primer coating standards. The plot is a typical predicted film thickness versus measured weight/area plot for multiple mid-IR readings on each standard for the calibration of mid-IR spectra versus film coating thickness according to an embodiment of the invention.

Referring to FIG. 2C is shown a conceptual exemplary calibration plot of a plurality of model mid-IR FT-IR spectroscopy measurements e.g., 205A, 205B, 205C taken from model standards with a known film coating (e.g., bond primer) thickness (e.g., $mg/ft^2$). The relative changes in absorbance and/or reflectance may be determined for each data point (relative change determined at selected one or more wavelengths) with respect to a reference sample spectrum (which may include an absence of, or a known thickness of the film coating) according to multivariate analysis. For example, each data point represents a relative change (at one or more wavelengths) in absorbance and/or reflectance compared to a reference IR spectrum e.g., taken from a reference sample without a film coating on a bare substrate or with a known thickness (or weight/area) of the film coating. The calibration regression analysis (line R) may be correlated with a separately determined thickness of the film coating (horizontal axis) e.g., $mg/ft^2$), as exemplified by a separate and independent thickness measurement, such as by optical or electron microscopy. It will be appreciated that the thickness may be expressed in terms of coating weight per unit area of film coating and used for this calibration as it is easier to measure in the process of making standards. It will further be appreciated that the coating thickness as expressed in weight per unit area may be easily transformed into conventional units of thickness e.g., mils.

It will also be appreciated that the model IR spectra with a model sample film coating may be simultaneously correlated with a compositional ingredient and a film thickness, since a mid-IR model spectrum may be used to determine a corresponding change in composition as well as thickness if the compositional ingredient that causes the relative changes in the spectrum is equally (isotropically) distributed through the thickness of the film.

Alternatively, one or more compositional ingredients and a film thickness may be separately correlated, such that one may independently determine a level of a compositional ingredient and a thickness of the film. For example it will be appreciated that a thickness (or weight/area) of the film may be separately determined by any established and calibrated means such as optical or electron microscopy measurements. It will be appreciated that the amount of one or more compositional ingredients of the film may be separately determined by any established and calibrated means such as chemical analysis, x-ray, or electron spectroscopy.

In one embodiment, the film coating may be a bond primer (organic containing material) that is formed on a metallic surface. For example, the metallic surface may be a titanium surface, such as a portion of an aircraft which may be bonded by use of the bond primer onto another portion of an aircraft, which may be a different material, including a polymer composite material. In some embodiments, the bond primer may contain chromium (chrome) where amounts of the chromium present may vary depending on the formulation of the bond primer and where the amount of chromium may be important to the performance of the bond primer. In addition, the metallic surface may be treated to form a roughened surface, such as by sand or grit blasting. It will be appreciated that having the correct coating thickness of the bond primer is critical to acceptable bond strength.

For example, by analyzing the data according to multivariate analysis (comparing sample IR spectra collected from a bond primer coated area of the roughened metallic surface with a reference spectra (e.g., the roughened metallic surface without bond primer), and then comparing the relative change in the sample IR spectra with a predetermined correlation of changes in model IR spectra correlated (calibrated) with a known change in the thickness and/or amount of chrome in the bond primer, a quantifiable thickness of the bond primer and/or amount of chromium in the bond primer may be determined. Thus, the quality or acceptability of the bond primer surface may be advantageously determined in real time with a hand-held portable IR spectrometer prior to bonding taking place in a manufacturing or maintenance process.

It will be appreciated that the method of the present invention is particularly advantageous when used to measure film coating thicknesses on roughened or uneven metal surfaces. For example, the roughness of the metal surface may include having variations in the surface topology up to about the thickness of the film coating, e.g., up to about 1 mil (0.001 inch).

For example, referring to FIG. 2C, is shown an exemplary conceptual predetermined calibration and prediction plot R representing a model validation method that leaves out one sample to make a model and uses that model to predict the sample omitted. This is done for each sample in order to build a predicted versus measured plot for FIG. 2C. The predetermined multivariate calibration automatically correlates the changes in IR spectroscopy measurements e.g., 205A, 205B, 205C, (where the relative change on the vertical axis in absorbance and/or reflectance is shown at a selected wavelength or group of wavelengths) and with the coating thickness or coating weight of the standards measured for the model.

Still referring to FIG. 2C, in one embodiment, a thickness range T may be imposed on the predetermined correlation (calibration) R, so that the IR spectroscopy measurements e.g., 205B and 205C can then be determined (estimated) to have a thickness within the proper range or thickness range T on the horizontal axis. For example, in one embodiment, an acceptable range for the bond primer thickness (weight/area) is in a range of about 220 to about 600 mg/ft$^2$. For example, in the exemplary sample IR spectroscopy measurements, e.g., 205B and 205C show a thickness within the thickness range T, and the thickness of the bond primer may be determined to be acceptable and the operator of the IR spectrometer notified by an audible and/or visual indication. Thus, the measurements 205B and 205C are determined in-situ and in real-time determined to represent an acceptable bond primer thickness following IR spectroscopic collection, multivariate prediction, and comparison to a predetermined thickness range T. On the other hand, measurement 205A may be determined to have an unacceptable bond primer thickness and the operator similarly notified. It will be appreciated that a similar in-situ measurement may be made to determine an appropriate or inappropriate level of a compositional ingredient (e.g., chrome).

In practice it has been found that the film thickness determination according to IR spectroscopy according to preferred embodiments of the invention for film thicknesses of about 0.15 to about 0.35 mils (thousandths of an inch) has an accuracy of about plus or minus 0.025 mil with respect to a separately performed thickness measurement (e.g., having an accuracy of equal to or greater than plus or minus 0.025 mil). For coating weight (weight per unit area of coating), the relevant coating weights of about 220 to about 600 mg/ft$^2$ have an accuracy of about +/−40 mg/ft$^2$ In one embodiment, the quantifiable level of the thickness and/or level of a compositional ingredient may include a separate spectroscopic measurement, such as in the UV and/or visible range of wavelengths that may be correlated with a separately and independently measured thickness and/or level of a compositional ingredient.

Figure 3:
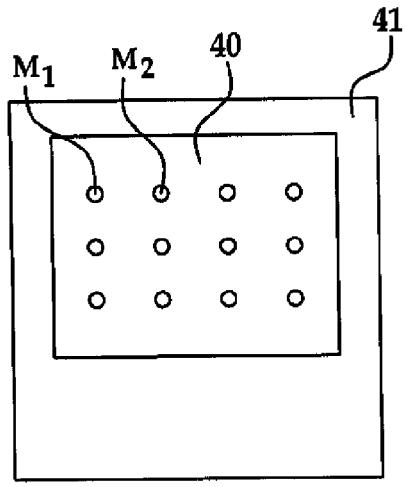
FIG. 3 shows an exemplary IR spectroscopy spot measurement process to map a film coating surface according to an embodiment of the invention.

Referring to FIG. 3, an exemplary IR spectroscopy measurement process is shown including an exemplary mapping of a film coating 40 on a roughened metallic surface 41 (underneath film coating 40). For example, following calibrating the IR spectrometer 10, a plurality of IR spectroscopy spot measurements e.g., M1, M2 (e.g., defined spot size of from 1 mm$^2$-10 mm$^2$) may be made sequentially or randomly over a predetermined area of the film coating surface. A thickness and/or composition map of the sample measurement area may be generated by mapping a determined thickness and/or composition with respect to each spot IR spectroscopy measurement and/or a running average thickness and/or composition may be sequentially determined over a defined measurement area for several IR spectroscopy measurements. It will be appreciated that the IR spectroscopy measurement spots e.g., M1, M2, may be any shape and where the noted spot sizes approximate a defined IR spectroscopic measurement area for an individual IR spectroscopy measurement.

Figure 4:
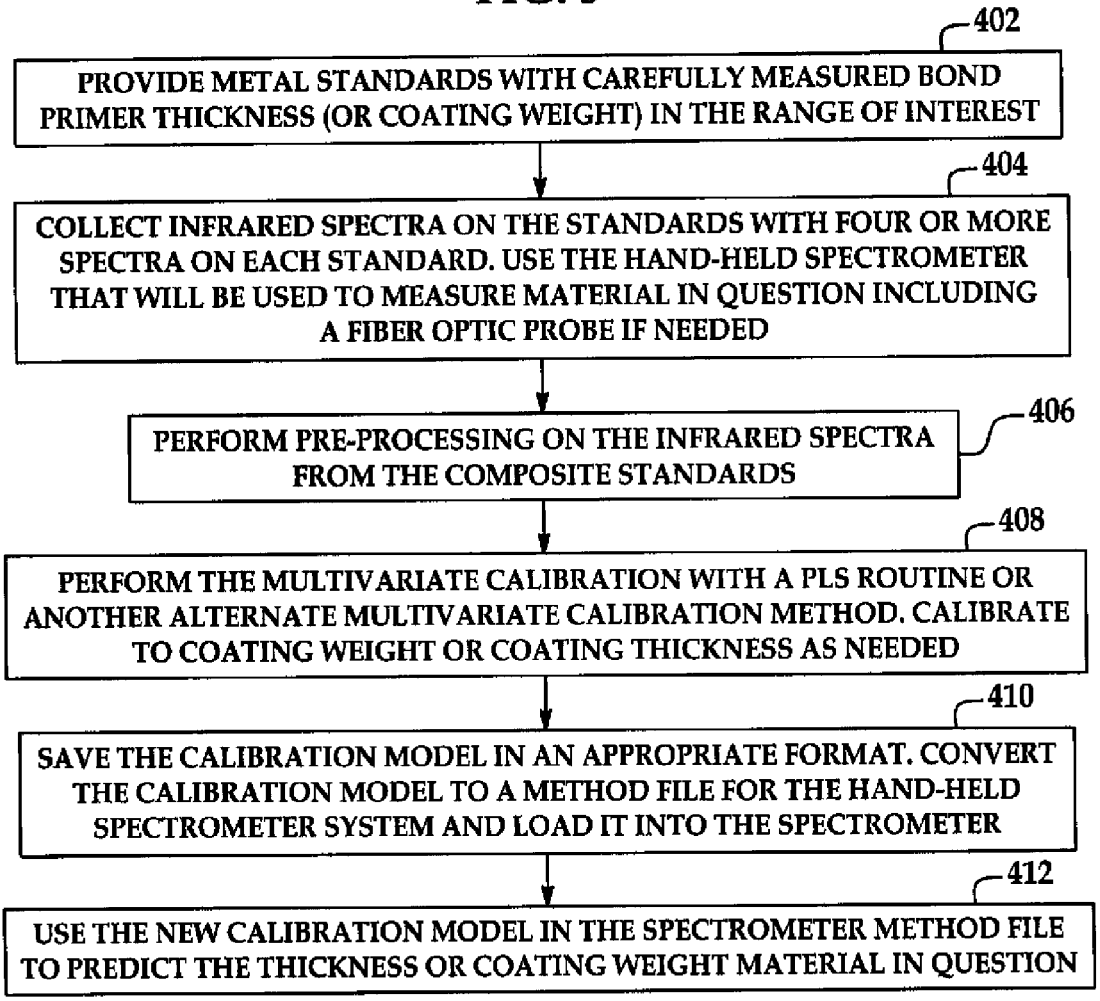
FIG. 4 is an exemplary process flow diagram including embodiments of the invention.

In an exemplary IR spectroscopy measurement process, referring to FIG. 4, in step 402 a series of coating thickness (e.g., weight/area) standards and/or one or more compositional ingredient standards are obtained for use in the calibration. In step 404 multiple IR spectra are collected on each standard (e.g., over mid-IR wavelength range e.g., 400-4000 wavenumbers (cm$^{-1}$) which may include using a reference sample with a bare substrate (e.g., metal) similar in surface topology (roughness) to the measurement samples to make an appropriate reference for the measurements. The coating standards must have a known thickness (e.g., weight/area) and/or known level of one or more compositional ingredients of the film coating on the substrate. A fiber optic probe may be used if need to reach hard to access measurement areas.

In step 406, the data pre-processing is performed on the spectra of the calibration standards in order to prepare the spectra for a good calibration model.

In step 408, a multivariate calibration model using a partial least squares (PLS) or another multivariate calibration method is made with the sample spectra and the known film coating thicknesses (e.g., weight/area) and/or a known level of one or more compositional ingredients determined by an independent measurement.

In steps 410 and 412, the calibration model is saved in a format that is useful for the hand-held spectrometer and it is down-loaded into the spectrometer system for use in predicting coating thicknesses (e.g., weight/area) and/or a level of one or more compositional ingredients for samples in question.

Figure 5:
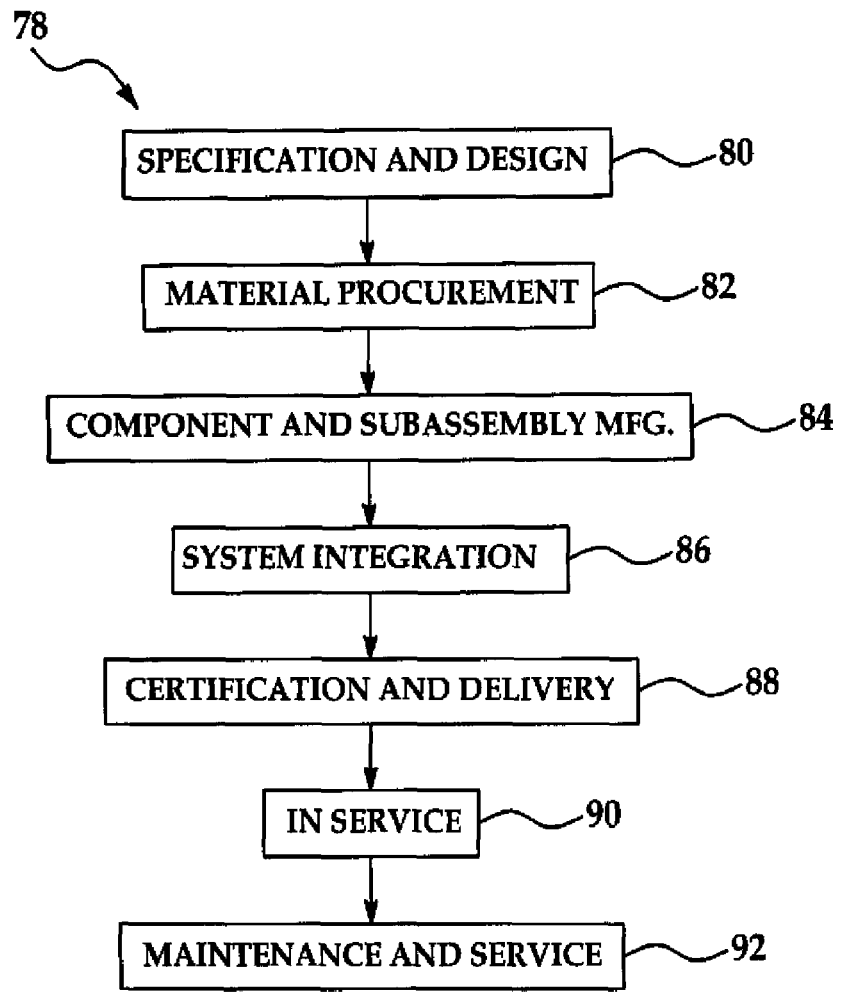
FIG. 5 is a flow diagram of an aircraft and service methodology according to an embodiment of the invention.
Figure 6:
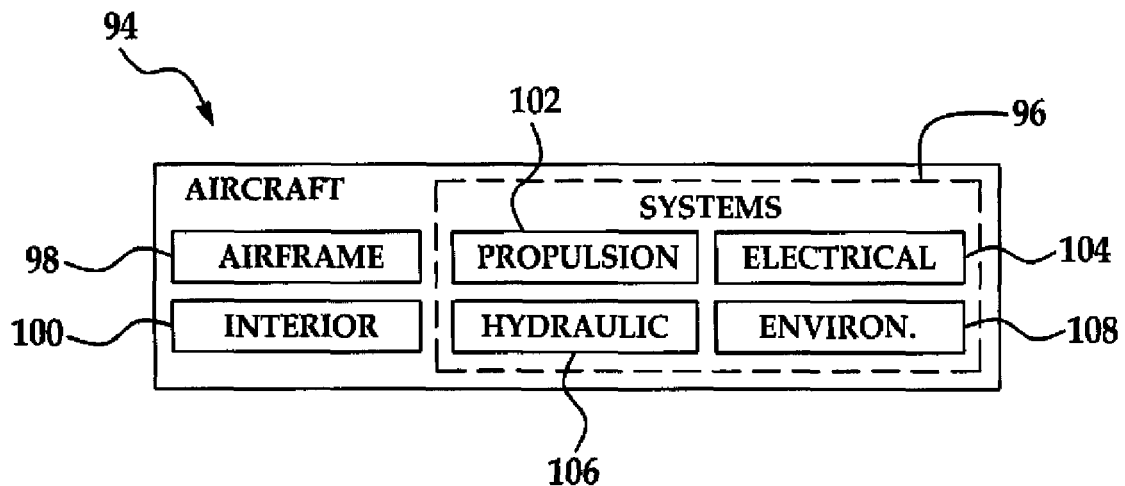
FIG. 6 is a block diagram of an aircraft according to an embodiment of the invention.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining a film coating thickness on a substrate and/or amount of one or more compositional ingredients of said film coating comprising:
   collecting a reference spectrum over a spectrum of infrared wavelengths from a reference sample wherein said thickness and/or amount of one or more compositional ingredients is present at a predetermined level, said collecting performed with an FT-IR spectrometer;
   obtaining a plurality of infrared spectroscopy spot measurements by randomly irradiating a predetermined area of said film coating on said substrate with infrared energy over said spectrum of wavelengths at a plurality of separate spots each having a spot size of from 1 mm$^2$ to 10 mm$^2$ on said film coating, said irradiating performed with FT-IR spectrometer;
   detecting said infrared energy reflected from said film coating on said substrate over said spectrum of wavelengths; said irradiating and said detecting steps are performed by a hand-held portable FT-IR spectrometer;
   performing multivariate analysis on the spectrum of said reflected infrared energy, said multivariate analysis comprising relative changes in said spectrum with respect to said reference spectrum;
   comparing results of said multivariate analysis with a predetermined calibration of model infrared energy spectra comprising said spectrum of wavelengths collected from a plurality of model film coatings, said model infrared energy spectra calibrated with respect to model film coatings comprising known film coating thickness and/or amount of one or more compositional ingredients; and,
   determining said thickness and/or amount of one or more compositional ingredients of said film coating and mapping said film coating according to said film coating thickness and/or amount of one or more compositional ingredients based on said predetermined calibration.

2. The method of claim 1, wherein said multivariate analysis comprises multivariate statistical approaches to determine said relative changes, said relative changes comprising absorbance and/or reflectance values at selected groups of wavelengths comprising said spectrum of wavelengths.

3. The method of claim 1, wherein said film coating comprises an organic containing material and said substrate comprises a metal.

4. The method of claim 1, wherein said film coating comprises a bonding primer and said substrate comprises a metal.

5. The method of claim 1, wherein said thickness and/or amount of one or more compositional ingredients in said model film coating is determined by an independent and separate measurement.

6. The method of claim 1, wherein said film coating thickness is determined to an accuracy of up to plus or minus 0.025 mil.

7. The method of claim 1, wherein said spectrum of wavelengths is from about 400 to about 4000 wavenumbers (cm$^{-1}$).

8. The method of claim 1, wherein said steps of irradiating and detecting are performed over a pre-determined area on said film coating.

9. The method claim 1, wherein said steps comprise a process selected from the group consisting of aircraft manufacturing, aircraft assembly, aircraft maintenance, and aircraft repair.

10. A method of determining a film coating thickness on a metallic substrate and/or amount of one or more compositional ingredients of said film coating using a portable hand-held FT-IR spectrometer comprising:
    collecting a reference spectrum over said spectrum of infrared wavelengths from a reference sample wherein said thickness and/or amount of one or more compositional ingredients is present at a predetermined level;
    positioning said portable hand-held FT-IR spectrometer to irradiate and detect reflected infrared energy over a spectrum of infrared wavelengths over a pre-determined area on said film coating;
    obtaining a plurality of infrared spectroscopy spot measurements by randomly irradiating a predetermined area of said film coating on said metallic substrate with infrared energy over said spectrum of wavelengths at a plurality of separate spots each having a spot size of from 1 mm² to 10 mm² on said film coating, said irradiating performed with said portable hand-held FT-IR spectrometer;

detecting said infrared energy reflected from said film coating on said metallic substrate over said spectrum of wavelengths, said detecting performed with said portable hand-held FT-IR spectrometer;

performing multivariate analysis on the spectrum of said reflected infrared energy, said multivariate analysis comprising relative changes in said spectrum with respect to a reference spectrum, said multivariate analysis performed with said portable hand-held FT-IR spectrometer;

comparing results of said multivariate analysis with a predetermined calibration of model infrared energy spectra comprising said spectrum of wavelengths collected from a plurality of model film coatings, said model infrared energy spectra calibrated with respect to model film coatings comprising known film coating thickness and/or amount of one or more compositional ingredients, said comparing performed by a processor comprising said hand-held FT-IR spectrometer; and, determining said thickness and/or amount of one or more compositional ingredients of said film coating and mapping said film coating according to said film coating thickness and/or amount of one or more compositional ingredients based on said predetermined calibration, said determining performed by a processor comprising said hand-held FT-IR spectrometer.

* * * * *